(12) United States Patent
Von der Haar

(10) Patent No.: US 7,235,788 B2
(45) Date of Patent: Jun. 26, 2007

(54) DETECTOR FOR A TOMOGRAPHY UNIT

(75) Inventor: Thomas Von der Haar, Nuernberg (DE)

(73) Assignee: Siemens Aktiengesellschaft, Munich (DE)

( * ) Notice: Subject to any disclaimer, the term of this patent is extended or adjusted under 35 U.S.C. 154(b) by 259 days.

(21) Appl. No.: 10/991,397

(22) Filed: Nov. 19, 2004

(65) Prior Publication Data
US 2005/0109946 A1 May 26, 2005

(30) Foreign Application Priority Data
Nov. 21, 2003 (DE) ................. 103 54 497

(51) Int. Cl.
*H01L 25/00* (2006.01)
*G01T 1/24* (2006.01)
(52) U.S. Cl. .............. 250/370.09; 250/363.05
(58) Field of Classification Search .......... 250/363.05, 250/370.09; 378/4
See application file for complete search history.

(56) References Cited

U.S. PATENT DOCUMENTS

| | | | |
|---|---|---|---|
| 4,338,521 A * | 7/1982 | Shaw et al. ........... 250/370.11 |
| 5,487,098 A * | 1/1996 | Dobbs et al. ................. 378/19 |
| 5,799,057 A * | 8/1998 | Hoffman et al. ............ 378/147 |
| 5,867,554 A | 2/1999 | Hupke |
| 6,055,296 A * | 4/2000 | Ferlic et al. ................. 378/154 |
| 6,115,448 A | 9/2000 | Hoffman |
| 6,137,859 A * | 10/2000 | Von Der Haar et al. ...... 378/19 |
| 6,144,718 A * | 11/2000 | Hoffman et al. ............. 378/19 |
| 6,587,538 B2 | 7/2003 | Igarashi et al. |
| 2002/0064252 A1* | 5/2002 | Igarashi et al. ............... 378/19 |
| 2004/0120448 A1* | 6/2004 | Ratzmann ....................... 378/4 |
| 2005/0161608 A1* | 7/2005 | Heismann .............. 250/370.09 |

FOREIGN PATENT DOCUMENTS

DE 19853646 5/1999

* cited by examiner

Primary Examiner—Albert Gagliardi
(74) Attorney, Agent, or Firm—Harness, Dickey & Pierce, P.L.C.

(57) ABSTRACT

A detector for a tomography unit, in particular an X-ray computer tomograph, includes a number of detector modules arranged next to one another in a z-direction and in a φ-direction running perpendicular thereto. In order to specify the adjustment, the detector modules bear against an adjusting plate on the beam input side. First adjusting devices are provided on the detector modules on the beam input side engaging with second adjusting devices, corresponding thereto and provided on the adjusting plate, for the purpose of accurately positioning the detector modules.

34 Claims, 2 Drawing Sheets

DETECTOR FOR A TOMOGRAPHY UNIT

The present application hereby claims priority under 35 U.S.C. §119 on German patent application number DE 103 54 497.6 filed Nov. 21, 2003, the entire contents of which are hereby incorporated herein by reference.

FIELD OF THE INVENTION

The invention generally relates to a detector for a tomography unit, in particular to an X-ray computed tomograph.

BACKGROUND OF THE INVENTION

A detector is known from EP 0 819 406 A1. The known detector is constructed from a number of modules both in the z-direction and in the φ-direction. This is a so-called multirow detector in which a number of rows of detector elements are arranged sequentially in the z-direction. This enables a number of images to be produced simultaneously in parallel sectional positions during a single measurement path.

In order to simplify the mounting, the detector elements are usually combined to form detector modules. In order to achieve the highest possible measuring accuracy, it is necessary for each detector module or collimator attached thereto on the beam input side to be aligned exactly with an X-ray machine arranged opposite the detector.

DE 101 58 021 A1 discloses a detector module that is composed of a collimator module and a sensor module. The detector module has lateral projections of opposing arrangement and with adjusting devices that cooperate with further adjusting devices, provided on a fastening frame, for accurately positioning the detector module on the frame. The proposed detector module is suitable for producing a detector in which in the z-direction only relatively few rows, that is to say four rows, are sequentially arranged.

DE 197 53 268 A1 describes a detector for an X-ray computed tomograph in which the collimator is designed in the form of thin metal plates that are mounted on a detector frame. An auxiliary device of comb-like design is provided for adjusting the metal plates.

In multirow detectors with a high number of rows, for example 16 rows, it has proved to be expedient in practice to attach a number of detector modules sequentially in the z-direction. It is necessary in this case to keep the interspaces between the detector modules as small as possible, in particular smaller than 300 μm. The accurate arrangement of such detector modules, and their precise adjustment to the focus of the X-ray machine require a relatively high outlay in practice.

SUMMARY OF THE INVENTION

It is an object of an embodiment of the invention to reduce or even eliminate at least one of the disadvantages of the prior art. In particular, an aim of one embodiment is to specify a detector for a tomography unit that can be produced with a reduced outlay. According to a further aim of an embodiment of the invention, it is to be possible to adjust detector modules of the detector as simply as possible.

According to an embodiment of the invention, it is provided that the detector modules bear against an adjusting plate on the beam input side, first adjusting device(s) provided on the detector modules on the beam input side engaging with second adjusting device(s), corresponding thereto and provided on the adjusting plate for the purpose of accurately positioning the detector modules. The proposed detector enables the detector modules to be accurately positioned with reference to a radiation source without great effort. In particular, it is possible to accurately adjust more than two detector modules arranged sequentially in the z-direction. This has the effect, in particular, of simplifying the production of a multirow detector.

The first adjusting devices are advantageously designed as projections extending from the detector module on the beam input side. The projections can be designed in the form of pins, webs, cones or pyramids. Of course, it is also possible for the projections to be designed in other suitable forms that preferably enable a self-centering arrangement. The term "self-centering" is understood to mean the accurate assumption of a prescribed position of the detector module with reference to a radiation source.

The second adjusting devices are advantageously cutouts designed to correspond to the first adjusting devices. In this case, the first adjusting devices can be brought into engagement with the second adjusting means by simply being plugged into the latter.

Each of the detector modules can be formed from a number of sensor elements that are arranged next to one another and are provided with a collimator on the beam input side. The sensor elements can be conventional sensor elements that are formed, for example, from a scintillator and a photodiode arranged downstream in the beam direction. In the case of such a detector module, the first adjusting devices can be connected to the collimator. The collimator can be formed from a holder that is preferably produced from plastic and in which collimator sheets are held, and the first adjusting means can be a constituent of the holder. By merely supplementing the holder with a first adjusting means, a detector module suitable for producing a detector according to an embodiment of the invention can be provided without great outlay.

The adjusting devices and the positioning plate are expediently produced from a material substantially transparent to x-ray radiation. The adjusting devices and the positioning plate are preferably produced from the same material. The adjusting devices and/or the adjusting plate can be produced from, preferably injection-molded, plastic. When selecting the plastic, it is to be ensured that it has the highest possible dimensional stability.

According to a further design refinement, the adjusting plate is held on a frame. The detector modules can be held between the adjusting plate and a retaining device situated opposite. This may be a plate with cutouts for feeding through cables or for connection of plug connectors. The detector modules are advantageously held bearing against the adjusting plate by means of the retaining device. For this purpose, elastic elements, for example springs, rubber elements, foam or the like, can be provided between the retaining plate and a rear side opposite the front side, on the beam input side, of the detector modules.

An embodiment of the invention also provides a tomography unit having a detector according to an embodiment of the invention.

BRIEF DESCRIPTION OF THE DRAWINGS

Exemplary embodiments of the invention are explained in more detail below on the basis of the drawing, in which.

DETAILED DESCRIPTION OF THE EXEMPLARY EMBODIMENTS

Figure 1:
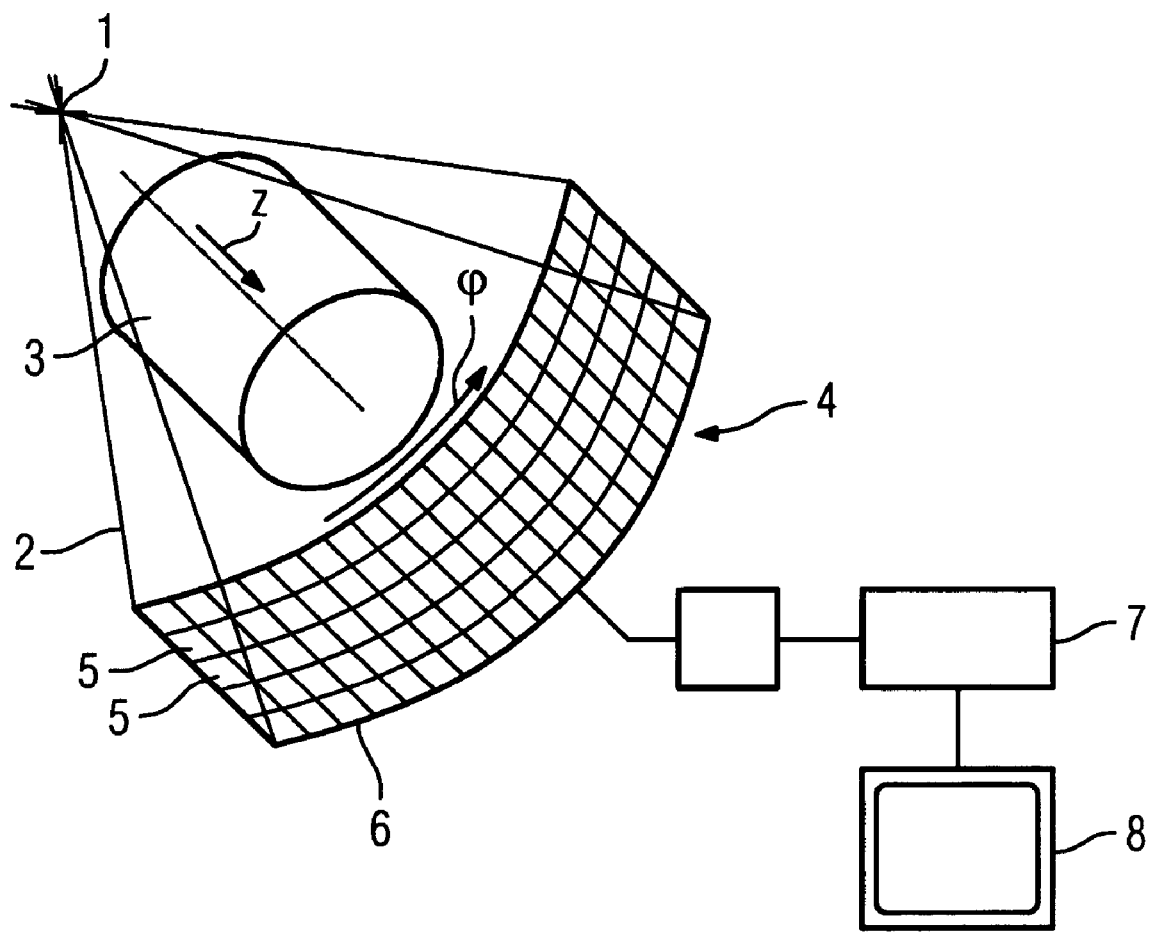
FIG. 1 shows a diagram of the design of an X-ray computed tomograph.

FIG. 1 shows a focus 1 of an X-ray machine from which there emanates a fan-shaped X-ray bundle 2 that is inserted through a diaphragm (not illustrated) and which permeates an object 3 and impinges on a detector 4. The detector 4 has a number of detector rows 5 arranged lying parallel to one another. The detector rows 5 are formed from a multiplicity of detector modules 6 lying next to one another.

The detector rows 5 are of arcuate design. The arc is denoted by φ. The detector rows 5 are arranged sequentially perpendicular to a z-direction. The z-direction runs parallel to a rotation axis of a rotatable measuring system comprising the detector 4 and the X-ray source.

The object 3 is irradiated from various projection angles as the measuring system rotates. A computer 7 uses the signals detected in this case by way of the detector 4 to calculate an image that is reproduced on a monitor 8.

Figure 2:
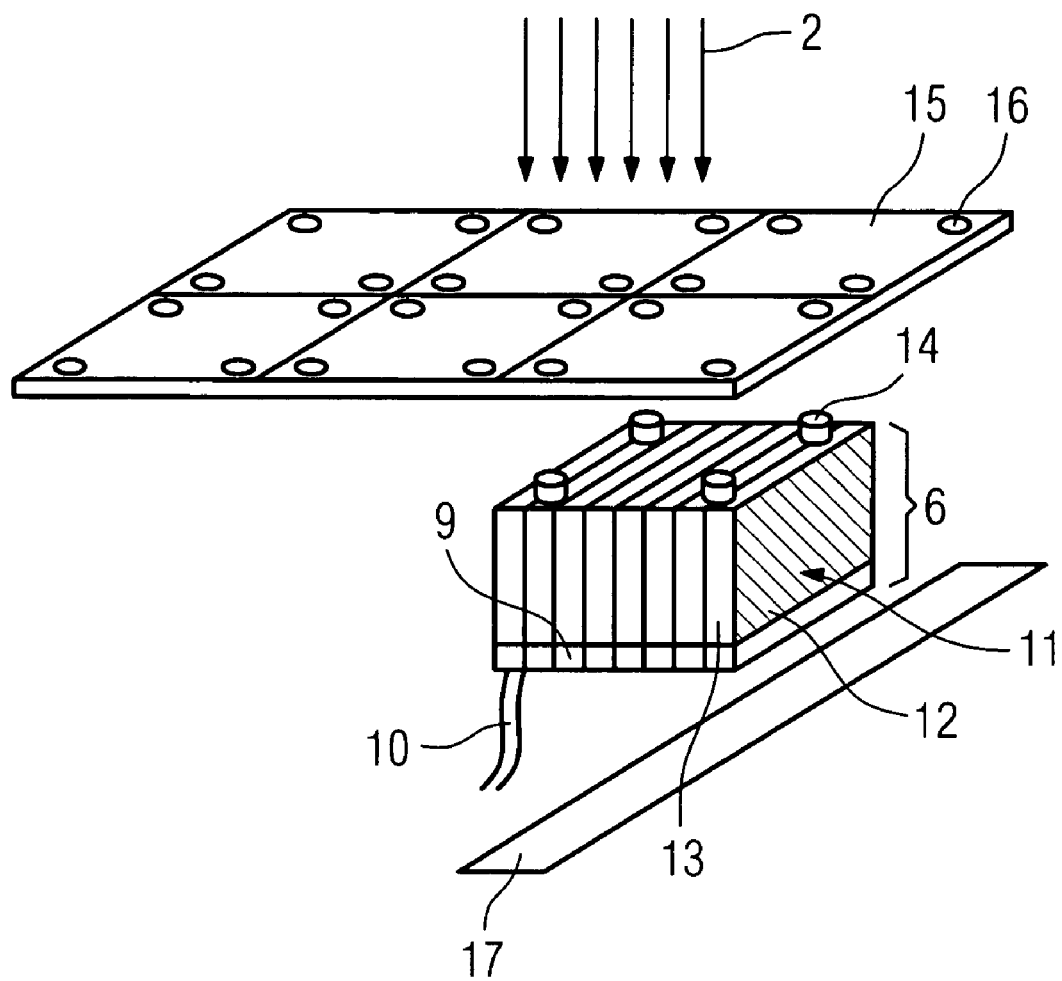
FIG. 2 shows a diagrammatic exploded illustration of a detector according to an embodiment of the invention.

FIG. 2 shows a diagrammatic exploded illustration of a section of a detector 4. The detector module 6 includes sensor elements 9 arranged sequentially in the φ-direction. A cable leading away from the detector element 6 is denoted by the reference numeral 10. A collimator 11 is arranged in front of the sensor elements 9 on the beam input side. The collimator 11 includes collimator sheets 12 arranged next to one another.

A holder 13 preferably produced from plastic fills up the interspaces formed between the collimator sheets 12. Extending from the holder 13 are pins 14 that are cylindrical in the direction of the beam input side. An adjusting plate 15, preferably produced from plastic, has cutouts 16 whose diameter corresponds to the diameter of the pins 14. A retaining plate 17 is located on a rear side opposite the front side, on the beam input side, of the detector module 6.

Figure 3:
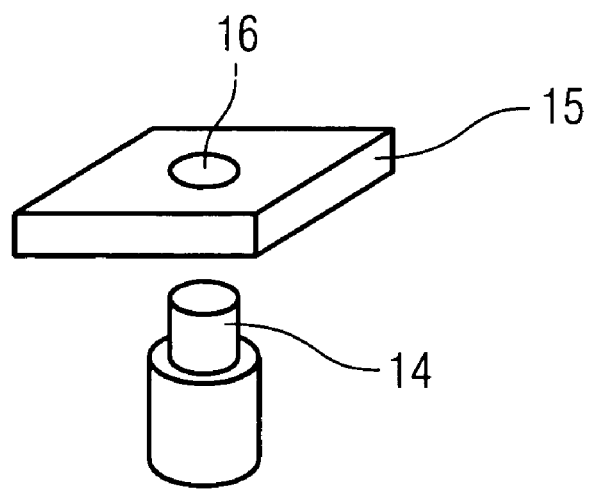
FIG. 3 shows a perspective view of positioning elements.

FIG. 3 shows a perspective view of a variant of a pin 14. This is a stepped pin. The height of the step is selected such that it is possible thereby to implement an exact adjustment of the detector element 6 to the focus 1 during positioning at the adjusting plate 15.

As may be seen from FIG. 2, in particular, the cutouts 16 are positioned with regard to their shape and arrangement such that the pins 14 extending from the detector module 6 can be plugged therein. In the plugged-in state, the detector module 6 is fixed in its position with reference to the adjusting plate 15.

In order to ensure that the detector modules 6 are held securely on the adjusting plate 15, they are held by way of the retaining plate 17 bearing against the rear side of the detector modules 6. This adjustment plate 15 and also the retaining plate 17 can be mounted on a frame (not shown here). The frame can be arcuately designed in a conventional fashion. Consequently, the adjusting plate 15 and the retaining plate 17 can also be of arcuate design.

In order to avoid undesired absorption of X-ray radiation the adjusting plate 15, the pins 14 and the holder 13 are produced from material such as plastic, transparent to X-rays. This material can be polypropylene, polyethylene or similar materials. It is also conceivable to produce the adjusting plate 15 from a metal, for example aluminum, with a low absorption coefficient.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector for a tomography unit, comprising:
   a plurality of detector modules arranged next to one another in a first direction and in a second direction, each of the plurality of detector modules including a plurality of first adjusting devices arranged on a beam input side; wherein the first and second directions are perpendicular; and
   an adjusting plate arranged on the beam input side of the plurality of detector modules, the adjusting plate including a plurality of second adjusting devices, each of the plurality of second adjusting devices being configured to engage with a corresponding one of the plurality of first adjusting devices to accurately position the detector modules.

2. The detector as claimed in claim 1, wherein the plurality of first adjusting devices are designed as projections extending from the plurality of detector modules on the beam input side.

3. The detector as claimed in claim 2, wherein the projections are designed in the form of at least one of pins, webs, cones and pyramids.

4. The detector as claimed in claim 3, wherein the plurality of second adjusting devices are cutouts designed to correspond with the plurality of first adjusting devices.

5. The detector as claimed in claim 3, wherein each of the plurality of detector modules is formed from a number of sensor elements, the sensor elements being arranged next to one another and being provided with a collimator on the beam input side.

6. The detector as claimed in claim 5, wherein the plurality of first adjusting devices are connected to the collimator.

7. The detector as claimed in claim 5, wherein the collimator is formed from a holder produced from plastic and in which collimator sheets are held, and wherein the adjusting plate is a constituent of the holder.

8. A tomography unit comprising the detector of claim 3.

9. The detector as claimed in claim 2, wherein the plurality of second adjusting devices are cutouts designed to correspond with the plurality of first adjusting devices.

10. The detector as claimed in claim 2, wherein each of the plurality of detector modules is formed from a number of sensor elements, the sensor elements being arranged next to one another and being provided with a collimator on the beam input side.

11. The detector as claimed in claim 10, wherein the plurality of first adjusting devices are connected to the collimator.

12. The detector as claimed in claim 10, wherein the collimator is formed from a holder produced from plastic and in which collimator sheets are held, and wherein the adjusting plate is a constituent of the holder.

13. A tomography unit comprising the detector of claim 2.

14. The detector as claimed in claim 1, wherein the plurality of second adjusting devices are cutouts designed to correspond with the plurality of first adjusting devices.

15. The detector as claimed in claim 1, wherein each of the plurality of detector modules is formed from a number of sensor elements, the sensor elements being arranged next to one another and being provided with a collimator on the beam input side.

16. The detector as claimed in claim 15, wherein each of the plurality of detector modules includes a collimator, and each of the plurality of first adjusting devices are connected to one of the collimators.

17. The detector as claimed in claim 15, wherein the collimator is formed from a holder produced from plastic and in which collimator sheets are held, and wherein the adjusting plate is a constituent of the holder.

18. The detector as claimed in claim 1, wherein the plurality of first and second adjusting devices and the adjusting plate are produced from a material substantially transparent to X-ray radiation.

19. The detector as claimed in claim 1, wherein at least one of the plurality of adjusting devices and the adjusting plate is produced from plastic.

20. The detector as claimed in claim 1, wherein the adjusting plate is held in a frame.

21. The detector as claimed in claim 1, wherein the plurality of detector modules are held between the adjusting plate and a retaining device situated opposite thereof.

22. The detector as claimed in claim 21, wherein the plurality of detector modules are held bearing against the adjusting plate by the retaining device.

23. A tomography unit comprising the detector of claim 1.

24. The detector as claimed in claim 1, wherein at least one of the plurality of adjusting devices and the adjusting plate is produced from injection-molded plastic.

25. The detector as claimed in claim 1, wherein the detector is for an X-ray computed tomograph.

26. A computed tomography unit comprising the detector of claim 25.

27. A computed tomography unit comprising the detector of claim 1.

28. The detector as claimed in claim 1, wherein the detector is for an X-ray computed tomograph.

29. A detector for a tomography unit, comprising:
- a plurality of detector modules;
- an adjusting plate arranged on a beam input side of the plurality of detector modules; and
- an adjusting means for accurately positioning the the plurality of detector modules, a portion of the adjusting means being arranged on a beam input side of the plurality of detector modules and a second portion of the adjusting means being arranged on the adjusting plate, the first and second portions of the adjusting means engaging with one another to accurately position the plurality of detector modules.

30. A tomography unit comprising the detector of claim 29.

31. A tomography unit comprising the detector of claim 30.

32. The detector as claimed in claim 29, wherein the first portion of the adjusting means includes projections extending from the detector modules on the beam input side.

33. The detector as claimed in claim 32, wherein the projections are designed in the form of at least one of pins, webs, cones and pyramids.

34. The detector as claimed in claim 29, wherein the plurality of detector modules are arranged next to one another in a first direction and a second direction, the first and second directions being perpendicular.

* * * * *